United States Patent [19]
Huband

[11] Patent Number: 5,254,100
[45] Date of Patent: * Oct. 19, 1993

[54] PROTECTIVE NEEDLE ASSEMBLY FOR HYPODERMIC SYRINGE

[76] Inventor: Michael L. Huband, 6513 Hagueman Dr., Richmond, Va. 23225

[*] Notice: The portion of the term of this patent subsequent to Apr. 14, 2009 has been disclaimed.

[21] Appl. No.: 856,377

[22] Filed: Mar. 23, 1992

Related U.S. Application Data

[63] Continuation-in-part of Ser. No. 711,652, Jun. 6, 1991, Pat. No. 5,104,385.

[51] Int. Cl.⁵ .............................................. A61M 5/32
[52] U.S. Cl. ..................................... 604/198; 604/263
[58] Field of Search ................ 604/198, 263, 192, 187

[56] References Cited

U.S. PATENT DOCUMENTS

| | | | |
|---|---|---|---|
| 4,695,274 | 9/1987 | Fox | 604/198 |
| 4,961,730 | 10/1990 | Poncy | 604/198 |
| 5,011,479 | 4/1991 | Le et al. | 604/198 |
| 5,053,018 | 10/1991 | Talonn et al. | 604/263 X |
| 5,104,385 | 4/1992 | Huband | 604/198 |

*Primary Examiner*—John D. Yasko
*Attorney, Agent, or Firm*—Norman B. Rainer

[57] ABSTRACT

A needle-protecting assembly adapted to be mounted upon the discharge extremity of the barrel of a conventional hypodermic syringe has a cylindrical hub adapted to hold a cannula needle of conventional construction. A transparent cylindrical sheath slidingly engages the hub. The sheath has a longitudinal slot and communicating detent, and a locking aperture. A tab radially emergent from the hub can be caused to engage the detent, slot or locking aperture, achieving respectively, a storage state where the sheath extends forwardly of the tip of the needle, a use state where the tip of the needle extends forwardly of the sheath, and an irreversibly locked disposal state wherein the sheath is forward of the tip of the needle.

6 Claims, 2 Drawing Sheets

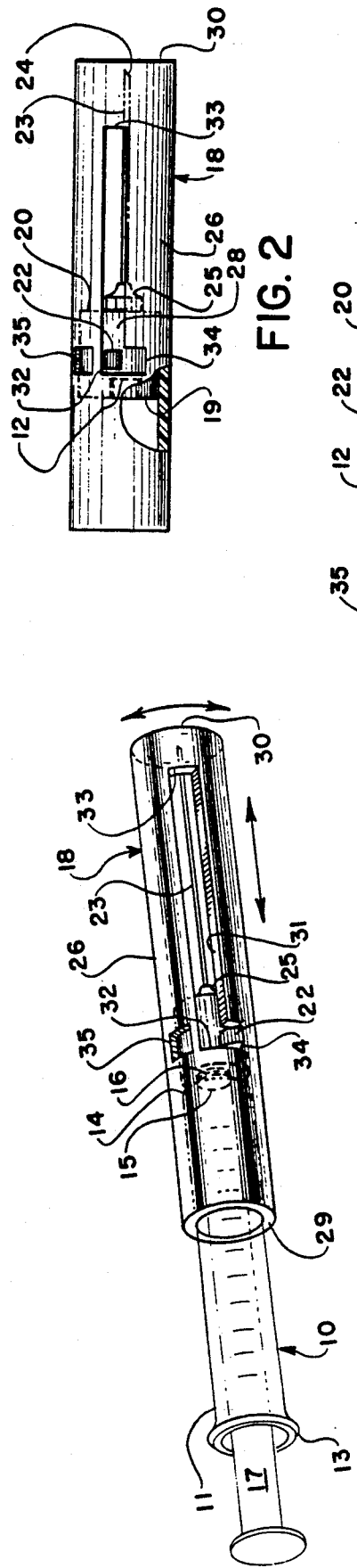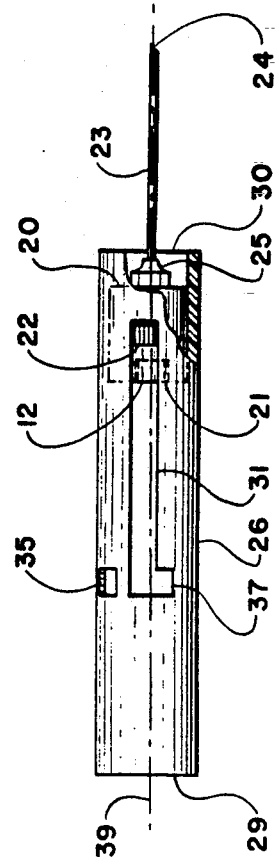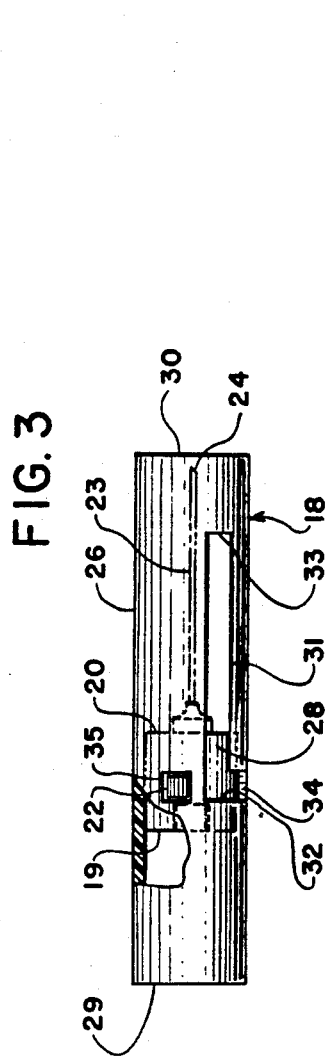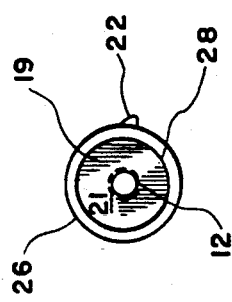
FIG. 1
FIG. 2
FIG. 3
FIG. 4
FIG. 5

PROTECTIVE NEEDLE ASSEMBLY FOR HYPODERMIC SYRINGE

RELATED APPLICATIONS

This application is a continuation-in-part of U.S. patent application Ser. No. 07/711,652, filed Jun. 6, 1991 now U.S. Pat. No. 5,104,385.

BACKGROUND OF THE INVENTION

1. Field of the Invention

This invention relates to a hypodermic syringe adapted to protect against accidental needle sticks.

2. Description of the Prior Art

Health professionals and others who use hypodermic syringes to inject medicine or other substances into patients or to obtain samples of blood or other bodily fluids from people are subject to risk of infection if they are stuck with a contaminated needle that has previously been used on an infected person. This is a matter of special concern when facing the possibility of dealing with patients who have infectious hepatitis or Acquired Immune Deficiency Syndrome (AIDS). The needle of a hypodermic syringe, being sharp to penetrate the skin readily for its intended purpose, can penetrate clothing and rubber gloves of the health professional using the hypodermic syringe and thus puncture the skin of the health professional. The threat of contamination is present with needles that are used for subcutaneous and intramuscular injection and needles used for intravenous injection of and for the drawing of blood or other body fluids from veins or other parts of the body. Likewise, hypodermic syringes used in dentistry also pose a threat of accidental contamination.

A hypodermic syringe is herein defined as a combination of a hollow needle or cannula having a pointed extremity and opposed mounting collar and a syringe comprised of a plunger slidingly interactive with a fluid-confining transparent barrel having an open rear extremity and apertured forward extremity equipped with a forwardly directed nipple adapted to engage the mounting collar of said needle. The barrel is typically marked with graduations to measure quantities of fluids injected or withdrawn. In some hypodermic syringes, designed for use in a vacuum withdrawal system or for dental use, the needle is normally double-ended, passing completely through the mounting collar and extending beyond the collar in both directions. The hypodermic syringe in such case serves as a support for a medication carpule having a soft plastic that is pierced by the needle, thereby enabling the plunger to dispense the contents of the carpule. In either event, the forwardly protruding pointed extremity of the needle is normally equipped with a removable cover to protect health professionals from accidental contact with the point of the needle.

For any of the uses described above, universal practice is either to discard the needle after one use, or else to sterilize it before another use. During the act of disposal, the contaminated needle is exposed between its site of use and a dispenser device. Carelessness on the part of the health professional or other user of the hypodermic, distractions occasioned by telephone calls and the like, or accidental jostling by a passersby, make it possible to bring the contaminated point of the needle into contact with the body of the health professional. A particular threat exists when the needle cover is replaced before the needle is discarded. In this case the health professional typically holds the needle cover in one hand and inserts the needle onto the cover. The same distracting factors may cause the contaminated point of the needle to come into contact with his or her hand.

U.S. patent application Ser. No. 07/711,652, filed Jun. 6, 1991 discloses a hypodermic syringe having a protective feature comprised of a hub which receives the rear extremity of the needle, and attaches to the nipple of the barrel. The hub further interacts with a cylindrical sheath in a manner whereby the point of the needle is protectively shielded following use. Although such innovation is highly effective, it has been found that manufacture of a needle whose rear extremity is embedded in a specialized hub is a very expensive endeavor.

It is accordingly an object of the present invention to provide apparatus for protectively covering the cannula needle of a hypodermic syringe before and after use of said syringe.

It is another object of this invention to provide apparatus as in the foregoing object wherein said cannula needle is of conventional design having a mounting collar.

It is a further object of the present invention to provide needle-protecting apparatus of the aforesaid nature which is simple to use and amenable to low cost manufacture.

These objects and other objects and advantages of the invention will be apparent from the following description.

SUMMARY OF THE INVENTION

The above and other beneficial objects and advantages are accomplished in accordance with the present invention by a needle-protecting assembly adapted for use with a conventional hypodermic syringe comprised of a barrel having a discharge extremity provided with needle-accepting means, said needle-protecting assembly comprising:

a) a hub having a circular cylindrical sidewall disposed upon a central axis, a forward extremity having forwardly directed coupling means for engaging a mounting collar of a conventional cannula, a rear extremity having a recess configured to engage said needle accepting means, a control tab radially emergent from said sidewall, and a passageway extending between said coupling means and recess along said axis, and b) a transparent cylindrical sheath elongated between forward and rearward rims and configured to slide upon said sidewall and envelope said hub, said sheath having: 1) a longitudinal slot extending in parallel relationship to said axis between a first extremity and a second extremity forwardly spaced from said first extremity, 2) a circumferentially disposed arcuate slot communicating with said first extremity, and 3) a locking aperture circumferentially separated from said arcuate slot, c) said sheath engaging said control tab in a manner whereby reciprocal axial motion of the sheath is permitted when said tab is in said longitudinal slot, and an irreversibly locked condition is produced when the tab is in said locking aperture, said locked condition characterized in disposing the forward rim of the sheath forwardly of the pointed extremity of said cannula.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing:

FIG. 1 is a perspective view of an embodiment of the needle-protecting assembly of the present invention in its storage or protected state and shown in functional association with a conventional hypodermic syringe and conventional cannula.

FIG. 2 is a side view of the embodiment of FIG. 1 in its ready to use state.

FIG. 3 is a side view of the embodiment of FIG. 1 in the deployed state of the cannula.

FIG. 4 is a side view of the embodiment of FIG. 1 in its locked, disposal state.

FIG. 5 is an end view of the embodiment of FIG. 1.

DESCRIPTION OF THE PREFERRED EMBODIMENT

Figure 6:
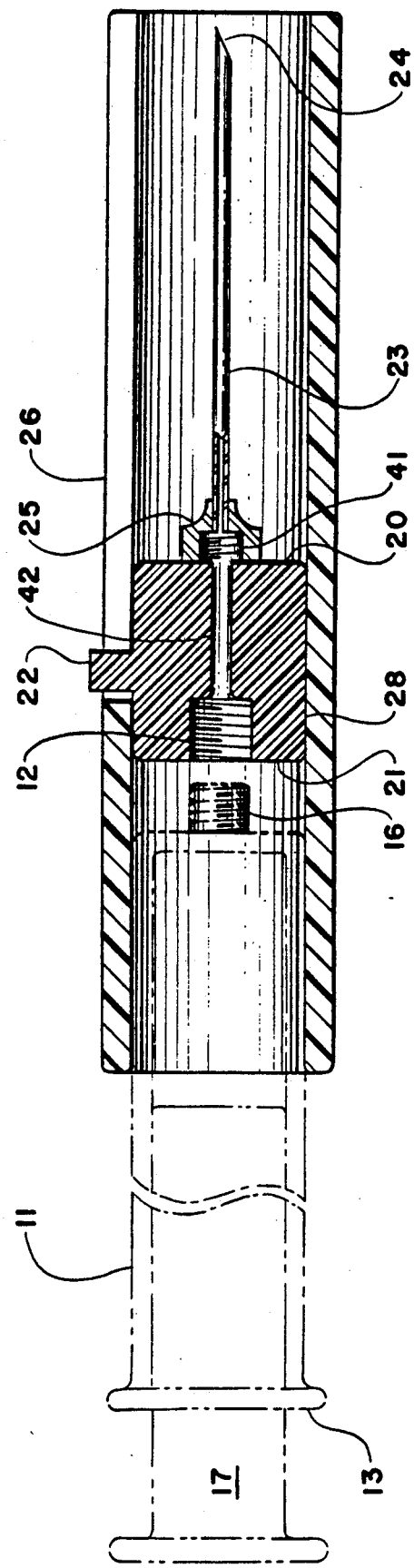
FIG. 6 is a longitudinal sectional view of the embodiment of FIG. 1.

Referring to FIGS. 1-6, an embodiment of the needle-protecting assembly of the present invention is shown adapted for use with common hypodermic syringe 10 comprised of elongated cylindrical barrel 11 having open receiving extremity 13, and discharge extremity 14 having centered aperture 15 and associated needle-accepting means in the form of threaded nipple 16. Elongated plunger 17 is adapted to reciprocate in close conformity within barrel 11.

Needle-protecting assembly 18 is comprised of monolithic cylindrical hub 19 defined in part by cylindrical sidewall 28 having a center axis 39 and a diameter slightly greater than the diameter of barrel 11. Said hub is further bounded by forward extremity 20 having forwardly directed threaded coupling means 41, and rear extremity 21 having threaded recess 12 centered on said axis and adapted to receive nipple 16 of barrel 11. Recess 12 may alternatively be configured to receive needle mounting means of conical shape which engage the hub by frictional effect. Similarly, coupling means 41 may be of conical shape. A passageway 42 communicates between forward and rear extremities 20 and 21 along said axis. A control tab 22 emerges radially from said sidewall.

Cannula needle 23 has a pointed forward extremity 24 and a rearwardly disposed mounting collar 25 which engages coupling means 41.

A transparent cylindrical sheath 26 elongated between forward and rearward rims 30 and 29, respectively is configured to slidingly embrace the hub, and attached needle by virtue of frictional interaction with sidewall 28 of said hub. The sheath has a longitudinal slot 31 extending in parallel relationship to said axis between a first extremity 32, and a second extremity 33 forwardly spaced from said first extremity. A circumferentially disposed arcuate slot 34 communicates at one terminus with said first extremity in an L-shaped intersection. The opposite terminus of slot 34, designated 37 serves as a retaining shoulder, or indent, as will hereinafter be shown. A locking aperture 35 is spaced apart from slot 34 in circumferential alignment therewith. The expression "transparent" as employed herein is intended to encompass sheaths fabricated of transparent plastic, and sheaths fabricated of opaque material but possessing slots that permit visual observation of the volumetric markings on the barrel of the hypodermic syringe.

In its stored or protective state, the needle-protecting assembly will be disposed as shown in FIG. 1 wherein tab 22 resides within retaining shoulder 37. In this configuration, the forward rim of the sheath extends forwardly of the pointed extremity of the needle. By twisting the sheath about the hub, tab 22 can be made to reside within slot 31, as shown in FIGS. 2 and 3. In this condition, a ready state, sheath 26 can undergo axially reciprocal movement in sliding engagement with the hub. At one extremity of said sliding movement, as shown in FIG. 3, substantially the entire length of sheath 26 is disposed upon barrel 11, causing the pointed extremity 24 of needle 23 to be exposed for use.

By sliding the sheath to its forward position and twisting about the axis, tab 22 enters locking aperture 35, producing the locked or disposal state of the assembly shown in FIG. 4. In said locked state, the sheath is immobilized in a position which protects the point of the needle. By causing the tab 22 to have a directional contour as a tapered gear tooth, entrance of said tab 22 into aperture 35 is irreversible, thereby preventing reuse of the needle and producing a protected condition for safe disposal.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A needle-protecting assembly adapted for use with a conventional hypodermic syringe comprised of a barrel having a discharge extremity provided with needle-accepting means, said needle-protecting assembly comprising:
   a) a hub having a circular cylindrical sidewall disposed upon a central axis, a forward extremity having forwardly directed coupling means for engaging a mounting collar of a conventional cannula having a pointed extremity, a rear extremity having a recess configured to engage said needle accepting means, a control tab radially emergent from said sidewall, and a passageway extending between said coupling means and recess along said axis, and
   b) a transparent cylindrical sheath elongated between forward and rearward rims and configured to slide upon said sidewall and envelope said hub, said sheath having: 1) a longitudinal slot extending in parallel relationship to said axis between a first extremity and a second extremity forwardly spaced from said first extremity, 2) a circumferentially disposed arcuate slot communicating with said first extremity, and 3) a locking aperture circumferentially separated from said arcuate slot,
   c) said sheath engaging said control tab in a manner whereby reciprocal axial motion of the sheath is permitted when said tab is in said longitudinal slot, and an irreversibly locked condition is produced when the tab is in said locking aperture, said locked condition characterized in disposing the forward rim of the sheath forwardly of the pointed extremity of said cannula.

2. The needle-protecting assembly of claim 1 further comprising a cannula having a mounting collar and pointed extremity, said cannula being associated with said assembly by way of engagement of said mounting collar with said mounting collar.

3. The needle-protecting assembly of claim 1 wherein said recess is threaded.

4. The needle-protecting assembly of claim 1 wherein said coupling means is threaded.

5. The needle-protecting assembly of claim 3 wherein said coupling means is threaded.

6. The needle-protecting assembly of claim 1 wherein said hub is of monolithic construction.

* * * * *